(12) United States Patent
Du et al.

(10) Patent No.: US 7,816,563 B1
(45) Date of Patent: Oct. 19, 2010

(54) METHOD FOR PREPARING HYPOCRELLIN

(75) Inventors: Minghui Du, Edmonton (CA); Darol Maunder, Edmonton (CA)

(73) Assignee: Alberta Innovates-Technology Futures, Edmonton, Alberta (CA)

( * ) Notice: Subject to any disclaimer, the term of this patent is extended or adjusted under 35 U.S.C. 154(b) by 0 days.

(21) Appl. No.: 12/633,595

(22) Filed: Dec. 8, 2009

(51) Int. Cl.
*C07C 45/00* (2006.01)
(52) U.S. Cl. ........................ 568/310; 568/315
(58) Field of Classification Search .............. 568/310, 568/315
See application file for complete search history.

(56) References Cited

U.S. PATENT DOCUMENTS 7,157,477 B2 * 1/2007 Zhang et al. ................ 514/357
2005/0143406 A1 * 6/2005 Miller ........................ 514/277

FOREIGN PATENT DOCUMENTS

WO        WO98/33470      * 8/1998

OTHER PUBLICATIONS

O'Brien et al. Perylenequinone Natural Products: Total Synthesis of Hypocrellin A. Journal of Organic Chemistry, 2010, vol. 75 (1), p. 57-68.*
Liu et al. Synthetic studies in novel hypocrellin B derivatives. Tetrahedron, 1993, vol. 49 (47), p. 10785-10792.*

* cited by examiner

*Primary Examiner*—Sikarl A Witherspoon
(74) *Attorney, Agent, or Firm*—King & Spalding

(57) ABSTRACT

Improved methods of preparing hypocrellin B from 4,9-dihydroxy-3,10-perylenequinones are described.

6 Claims, No Drawings

METHOD FOR PREPARING HYPOCRELLIN

FIELD OF INVENTION

The present invention relates to methods of preparing hypocrellin, more particularly, methods of preparing hypocrellin B from perylenequinones such as phleichrome.

BACKGROUND OF THE INVENTION

Hypocrellins are naturally occurring perylenequinones found in various parasitic fungi, including *Hypocrella bambusae* and *Shiraia bambusicola*. The photosensitizing activity and chemical structure of hypocrellin B and a related compound hypocrellin A was first described in 1992 (Nenghui et al., 1992, *J. Photochem Photobiol B* 14(3):207-17). These and other related hypocrellins (C, D) and perylenequinones have subsequently been identified in other species of fungi. Phleichrome, a perylenequinone, is a known natural product initially isolated from the mycelium of *C. phlei*.

Hypocrellins and fungal perylenequinones have been investigated for their use as photodynamic therapy (PDT) agents, antiviral, anticancer, antimicrobial and antiparasitic activities and the like (Ma et al., 2004 Antimicrobial Agents and Chemotherapy 48:4450-4452) and derivatives exhibiting enhanced absorption at specific wavelengths (for PDT applications) have been developed (see, for example, Paul et al., 2008. J. Photochem. Photobiol B 94:38-44). The availability of hypocrellins and fungal perylenequinones for these uses however, is limited by extraction from the fungi that produce it, or complex multi-step synthetic methods from precursors (PCT Publication WO 98/33470, U.S. Pat. No. 6,936,571, Hauser et al., 1994 J. Org Chem 59:1697-1969). Diwu et al., 1992 (Tetrahedron 48:45-54) describes a one-step coupling reaction to produce perylenequinone from 1,2 naphthoquinone.

*H. bambusae* has not been reported as successfully grown in culture, thus its role as a source of hypocrellin is limited to its harvest in China. Other fungi that produce perylenequinones have been successfully grown in culture. For example, Seto et al (2005, Biosci. Biotechnol. Biochem 69(8):1515-1519; which is incorporated herein by reference) observed that Timothy plants infected by the fungus *Epichloe typhina* are resistant to disease caused by the *C. phlei* fungus, and identified metabolites (cyclo-(L-Pro-L-Leu) and cyclo-(L-Pro-L-Phe) that stimulate *C. phlei* to produce phleichrome. A publication by Lee et al., (2007, Biotechnology and Bioprocess Engineering 12:505-518; which is incorporated herein by reference) describes culture conditions and extraction of phleichrome from *C. phlei*. A recent publication by Kim et al. (2009, Plant Pathol J. 25:179-183; which is incorporated herein by reference) has described a transformation protocol for genetic manipulation of *C. phlei*, which may be useful for development of fungal strains that are enhanced for production of phleichrome or other perylenequinones.

Synthesis of hypocrellin B from precursors is complicated as illustrated by PCT publication WO 98/33470; and extraction from natural sources may not provide sufficient product for widespread use in pharmaceuticals. A more expedient method of obtaining hypocrellin B would be advantageous.

SUMMARY OF THE INVENTION

The present invention relates to methods of preparing hypocrellin, more particularly, methods of preparing hypocrellin B from perylenequinones such as phleichrome.

It is an object of the invention to provide an improved method for preparing hypocrellin.

The present invention provides for a method of preparing hypocrellin B comprising: combining a 4,9-dihydroxy-3,10-perylenequinone with an oxidation reagent to provide an oxidation product of phleichrome; and cyclization of the oxidation product to provide hypocrellin B.

The 4,9-dihydroxy-3,10-perylenequinone may be phleichrome.

The oxidation reagent may comprise DMSO and acetic anhydride. The cyclization step may occur under basic reaction conditions. In some embodiments, the cyclization step comprises combining the oxidation product with an alkali hydroxide; in some embodiments, the alkali hydroxide is LiOH.

It is therefore an advantage of some aspects of the present invention to provide a one-step method of preparing hypocrellin B from phleichrome. Such a method represents an improvement over obtaining hypocrellin B from the tree fungus *H. bambusae*, which has limited geographical and seasonal availability. Such a method also represents an improvement over a multi-step synthesis of hypocrellin B from precursors by reducing the number of steps and quantity of reagents consumed.

This summary of the invention does not necessarily describe all features of the invention. Other aspects, features and advantages of the present invention will become apparent to those of ordinary skill in the art upon review of the following description of specific embodiments of the invention.

DETAILED DESCRIPTION

The present invention relates to methods of preparing hypocrellin, more particularly, methods of preparing hypocrellin B from perylenequinones such as phleichrome.

As an example, a method of preparing hypocrellin B from 4,9-dihydroxy-3,10-perylenequinone is provided.

Examples of 4,9-dihydroxy-3,10-perylenequinones include phleichromes, cercosporin, fagopyrin, altertoxin, hypericin, elsinochromes and the like. These compounds are produced by various fungi or plants—generally the compound is named after the fungi or plant from which it was isolated and studied. For example, cercosporin may be obtained from an extraction of *Cercospora* spp.; phleichrome may be obtained from an extraction of *Cladosporium phlei*.; altertoxin may be obtained from an extraction of *Alternaria laternata*; elsinochrome may be obtained from an extraction of *Elsinone* spp.; hypericin may be obtained from an extraction of *Hypericum perforatum*; fagopyrin may be obtained from an extraction of *Fagopyrum sagittatum*. See, for example, Daub et al. 2000 Annu. Rev Phytopathol 38:461-90; Kim et al., supra; Li et al., 2001 J. Food Prot 64:567-71; Ma et al., 2003. World J Gastroenterol 9:485-90; Hinneburg et al. 2005. 53:3-7; Poutaraud et al., 2001 Phytochem Anal 12:355-62.

*C. phlei* may be cultured by known methods and the phleichrome pigment obtained by extraction of the mycelial mass, culture medium or both the mycelial mass and culture medium, according to known methods (see, for example Lee et al., 2007, Biotechnology and Bioprocess Engineering 12:505-518; which is incorporated herein by reference). The *C. phlei* fungus may also be genetically manipulated to alter natural pigment production (see, for example, Kim et al., 2009, Plant Pathol J. 25:179-183; which is incorporated herein by reference). Alternately, phleichrome may be obtained by synthesis, as described for example the method of Broka, 1991 (Tetrahedron Letters 32:859-862, which is incorporated herein by reference) or of Coleman and Grant 1995. (J. AmChem Soc 117:10889-10904, which is incorporated herein by reference).

Phleichrome may be purified to the desired degree of purity, for example from about 30 to about 99% purity, or any amount therebetween, using known purification techniques.

Oxidation of Phleichrome and Cyclization

Once phleichrome is obtained, the secondary alcohol groups of phleichrome (1; see structure below) may be oxidized to yield the corresponding ketone (2). Examples of oxidizing reagents include DMSO, Collins' reagent, Corey's reagent, pyridinum dichromate, $Na_2Cr_2O_7$ in water, $K_2Cr_2O_7$ in DMF (with heat), $CrO_3$ on a silica support (e.g. silica gel) or the like. Such reagents and conditions for their use are described in, for example, *March's Advanced Organic Chemistry* (M B Smith and J March, eds. Wiley & Sons, 5$^{th}$ edition 2001 chapter 19-3; which is incorporated herein by reference) and references therein.

In some embodiments, oxidation of a secondary alcohol may be performed using DMSO in combination with DCC and anhydrous phosphoric acid, oxalyl chloride, acetic anhydride, methanesulfonic anhydride, tosyl chloride, $P_2O_5$-$Et_3N$, trichloromethyl chloroformate, KI and $NaHCO_3$, and the like.

In some embodiments, the oxidation of phleichrome is performed using DMSO in combination with acetic anhydride (Albright-Goldman oxidation) to produce compound (2). Such an oxidation is exemplified in step 1 of Scheme 1 (outlined in Example 1). Acetic anhydride may be used with about 3 to 6 equivalents of acetic anhydride, or about 4, or about 5 equivalents. In some embodiments, acetic anhydride may be used in a significantly greater excess, from about 6 to about 10, to about 20 or more equivalents; for example about 6, 7, 8, 9, 10, 11, 12, 13, 11, 15, 16, 17, 18, 19, 20 equivalents. The oxidation may be performed at ambient (room) temperature, or heat may be applied and the oxidation performed at about 20, 25, 30, 25, 40, 45, or 50 degrees Celsius, or any temperature therebetween.

The compound (2) is subsequently cyclized to yield the product hypocrellin B (3). In some embodiments this may be via an intramolecular Aldol condensation. The cyclization reaction may comprise combining compound (2) with either LiOH in methanol-water, or 10% NaOH at ambient temperature, for 1-6 hours.

In some embodiments, the reaction of step 1 is conducted under conditions sufficient to permit the cyclization to occur spontaneously (see, for example Scheme 2).

Uses of Hypocrellin B

Hypocrellin B may be used in various applications. For example, it may be used as a starting compound for synthesis of other perylenequinones (WO 98/44470). Derivatives of hypocrellin B, including monomer ruthenium complexes, may be produced for use as photodynamic therapy agents (Paul et al., 2009. J. Photochem Photobiol B 94:38-44; Zhou et al., 2005. Bioorganic and Medicinal Chemistry Letters 15:3067-3070).

Photodynamic agents such as hypocrellin B or a derivative thereof may be coupled to an antibody or another binding agent that specifically binds a tumor or microbe (for example, WO 2001/012217, WO 2004/044191). Hypocrellin B or a derivative thereof may be useful as an as a sonosensitizer and/or a photosensitizer (for example WO 2002/060483, WO 2003/063901), and, when activated by light, modulate the activity of an immunotherapeutic agent (for example, WO 2002/060482).

Uses and derivatives reference herein are for example purposes—other uses for hypocrellin B and/or derivatives thereof will further be apparent to those of skill in the relevant art.

The present invention will be further illustrated in the following examples. However it is to be understood that these examples are for illustrative purposes only, and should not be used to limit the scope of the present invention in any manner.

Example 1

Two Step Chemical Conversion of Phleichrome to Hypocrellin B

Oxidation by DMSO/Acetic Anhydride (Albright-Goldman Oxidation) Followed by Cyclization with LiOH or NaOH (Scheme 1)

Phleichrome (1) was produced and extracted from *C. phlei* mycelial mass as described by Lee et al. (2007, Biotechnology and Bioprocess Engineering 12:505-518). Biomass was extracted with ethyl acetate or dichloromethane. The dark colored residue left upon evaporation of organic solvents was purified on silica gel using 1-5% MeOH-dichloromethane as eluent.

A solution of Phleichrome (200 mg) in DMSO (4 mL) and acetic anhydride (2 mL) was heated at 40° C. for 24 h. The reaction mixture was diluted by dichloromethane, washed with water and evaporated to produce a crude product (2) (1,12-Bisacetonyl-2,6,7,11-tetramethoxy-4,9-dihydroxy-3,10-perylenedione). The crude product (2) was used in the following cyclization reaction without further purification.

1. Cyclization with LiOH

A solution of the crude product (2) in methanol (10 mL) was cooled to 0° C., and LiOH (700 mg) in water (2 mL) was added. The mixture was stirred at room temperature for 4 h and acidified with 8% HCl to a pH of approximately 4. The mixture was extracted with dichloromethane, and the solvent evaporated. The extracted product was purified on silica gel using methanol-dichloromethane 1-5% as eluent to obtain hypocrellin B (product (3); 81 mg, ~40%, two steps) as a dark purple solid. The thin layer chromatographic profile (methanol-dichloromethane 5%) and $^1$H-NMR was identical to that of Hypocrellin B extracted from *H. bambusae*. $^1$H NMR ($CDCl_3$): δ 6.44, 6.42 (2s, 2H, ArH), 4.15, 4.09, 4.05 (4s, each 3H, 4 $OCH_3$), 4.04, 3.22 (dd, 2H, $J_{AB}$=11.5 Hz, $CH_2$), 2.37, 1.85 (2s, each 3H, 2$CH_3$). LC-MS: 529 (M+H).

2. Cyclization with NaOH

The crude product (2) was dissolved in 10% sodium hydroxide (10 mL) and stirred for 1 h. The aqueous solution was extracted with dichloromethane and then acidified with 2M HCl to a pH of approximately 4. The mixture was then extracted with dichloromethane and extract purified on silica gel column (methanol-dichloromethane 1-5%) to provide Hypocrellin B (product, (3); 70 mg, ~35%). Thin-layer chromatography results and $^1$H-NMR were identical to that obtained from naturally occurring and extracted Hypocrellin B from *H. bambusae*, and as obtained by cyclization product using LiOH as outlined above.

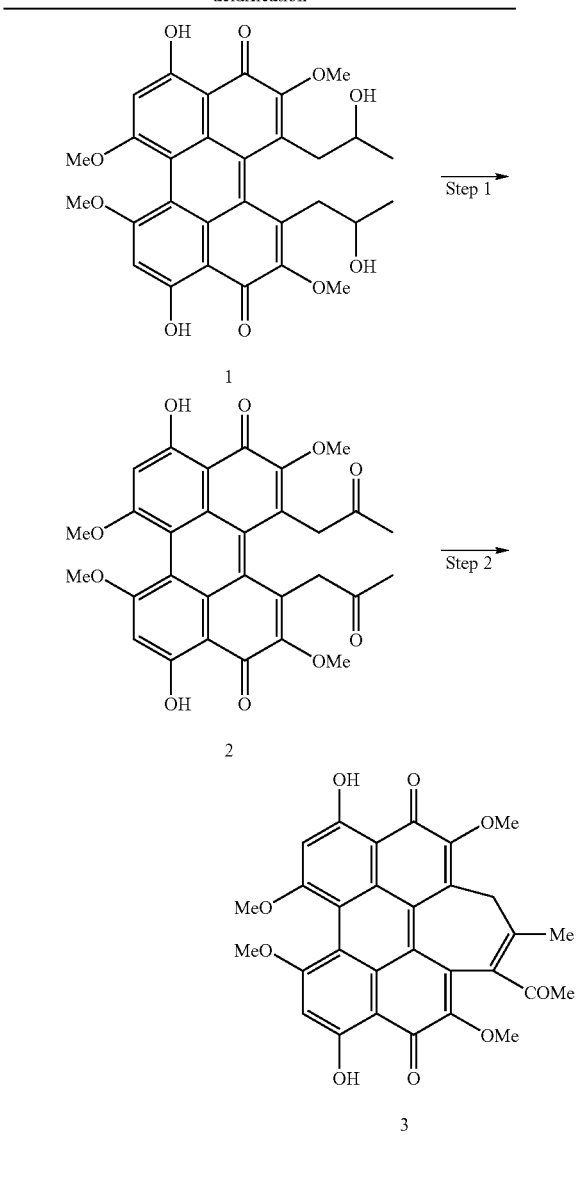

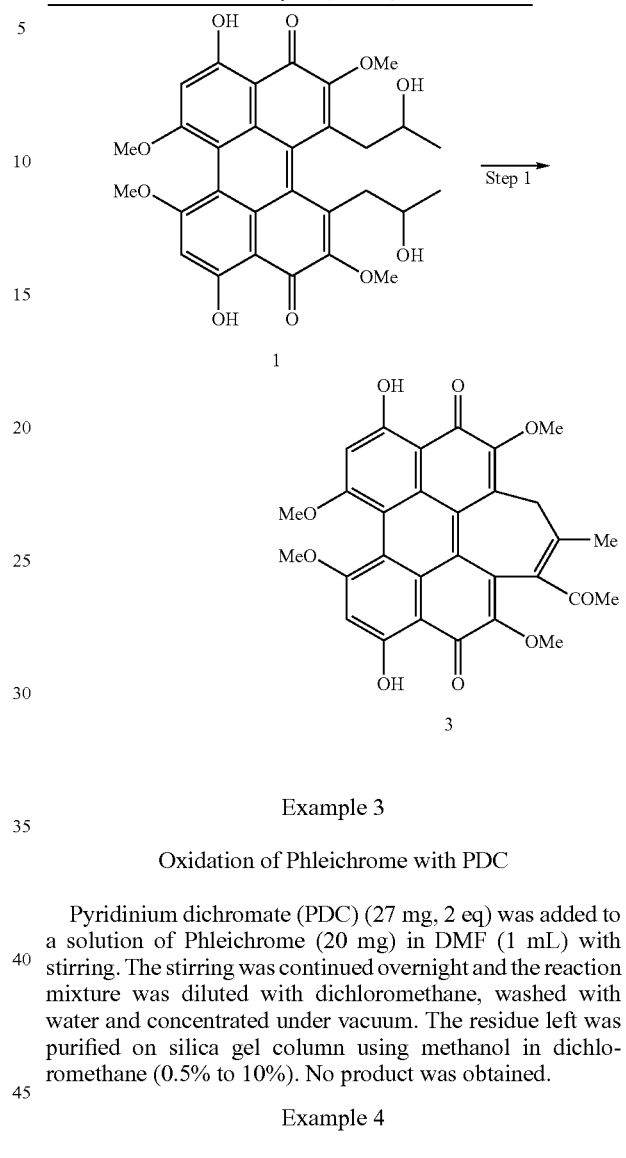

Example 2

One Step Chemical Conversion of Phleichrome to Hypocrellin B (Scheme 2)

A solution of Phleichrome (100 mg) in DMSO (2 mL) and acetic anhydride (1 mL) was heated at 40° C. for 24 h. The reaction mixture was diluted by dichloromethane (15 mL), washed with water and evaporated. The residue was chromatographed on two silica gel columns (1-5% MeOH-dichloromethane) to provide Hypocrellin B (25 mg, ~25%). Thin-layer chromatography results and $^1$H-NMR were identical to that obtained from naturally occurring and extracted Hypocrellin B from *H. bambusae*, and as obtained by the two-step chemical conversion (Scheme 2).

Example 3

Oxidation of Phleichrome with PDC

Pyridinium dichromate (PDC) (27 mg, 2 eq) was added to a solution of Phleichrome (20 mg) in DMF (1 mL) with stirring. The stirring was continued overnight and the reaction mixture was diluted with dichloromethane, washed with water and concentrated under vacuum. The residue left was purified on silica gel column using methanol in dichloromethane (0.5% to 10%). No product was obtained.

Example 4

Oxidation of Phleichrome by DMSO/Oxalyl Chloride (Swern Oxidation) Followed by Cyclization with LiOH DMSO (0.10 mL) was added to a stirred solution of oxalyl chloride in dichloromethane (0.477 mL, 1.9 M) at −60° C. After 5 min of stirring, the solution was added to phleichrome (50 mg) in dichloromethane (0.5 mL) at 0° C. Stirring was continued for 2 h until tlc (10% MeOH in dichloromethane) showed all starting material disappeared. Triethylamine (0.5 mL) was added and the reaction mixture was concentrated to remove solvent.

The remaining residue was dissolved in MeOH (5 mL) and to this mixture was added LiOH (600 mg) in water (6 mL) at 0° C. Stirring was continued for 3 h at room temperature and acidified with 8% HCl. Extraction with dichloromethane and evaporation of the solvent left a dark residue which was purified on silica gel using methanol-dichloromethane 1-5% as eluent. A product was obtained, however $^1$H-NMR analysis demonstrated that the product was not Hypocrellin B.

Example 5

Oxidation by DMSO/Methanesulfonic Anhydride Followed by Cyclization with LiOH A solution of Phleichrome (50 mg) in DMSO (1 mL) and methanesulfonic anhydride (160 mg) was stirred for 24 h. The reaction mixture was diluted by dichloromethane, washed with water and evaporated. The crude product was used in the following cyclization reaction without further purification.

To a solution of the above crude product in methanol (2 mL) cooled at 0° C. was added LiOH (150 mg) in water (0.15 mL). The mixture was stirred at room temperature for 4 h and acidified with 8% HCl. Extraction with dichloromethane and evaporation of the solvent left the crude product which was purified on silica gel using methanol-dichloromethane 1-5% as eluent. No product (Hypocrellin B) was obtained (verified by 1H NMR and thin layer chromatography).

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. A method of preparing hypocrellin (B) comprising:
   obtaining a 4,9-dihydroxy-3,10-perylenequinone;
   combining the 4,9-dihydroxy-3,10-perylenequinone with an oxidation reagent to provide an oxidation product of the 4,9-dihydroxy-3,10-perylenequinone; and
   cyclization of the oxidation product to provide hypocrellin B.

2. The method of claim 1 wherein the 4,9-dihydroxy-3,10-perylenequinone is phleichrome.

3. The method of claim 1 wherein the oxidation reagent comprises DMSO and acetic anhydride.

4. The method of claim 1 wherein the cyclization step occurs under basic reaction conditions.

5. The method of claim 1 wherein the cyclization step comprises combining the oxidation product with an alkali hydroxide.

6. The method of claim 5 wherein the alkali hydroxide is LiOH or NaOH.

* * * * *